United States Patent
Kono et al.

[19]

[11] Patent Number: 5,880,359
[45] Date of Patent: Mar. 9, 1999

[54] CONTAINER INSPECTING APPARATUS

[75] Inventors: Tadahisa Kono; Masaji Nishimura; Kunihiko Kubota; Yasuo Miwa, all of Yokohama, Japan

[73] Assignee: Kirin Techno-System Corporation, Yokohama, Japan

[21] Appl. No.: 900,126

[22] Filed: Jul. 25, 1997

[30] Foreign Application Priority Data

Jul. 26, 1996 [JP] Japan ................................. 8-215303
Dec. 16, 1996 [JP] Japan ................................. 8-353173

[51] Int. Cl.⁶ ........................... G01N 21/90; G01N 29/00
[52] U.S. Cl. ................................. 73/49.3; 73/52
[58] Field of Search ..................... 73/52, 40, 41.2, 73/41.3, 41.4, 45, 45.4, 49.3

[56] References Cited

U.S. PATENT DOCUMENTS 3,608,715  9/1971  Synder et al. ......................... 73/52 X

FOREIGN PATENT DOCUMENTS

| 0 240 432 | 10/1987 | European Pat. Off. |  |
|---|---|---|---|
| 0 269 815 | 6/1988 | European Pat. Off. | 73/52 |
| 540853 | 5/1993 | European Pat. Off. | 73/52 |
| 2 126 301 | 12/1972 | Germany | 73/52 |
| 55-122129 | 9/1980 | Japan | 73/45.4 |
| 02-54141 | 2/1990 | Japan | 73/52 |
| 06-174578 | 6/1994 | Japan | 73/52 |
| 06-105198 | 12/1994 | Japan | 73/49.3 |
| WO 85/00123 | 1/1985 | WIPO |  |
| 5250 | 4/1991 | WIPO | 73/52 |

*Primary Examiner*—Daniel S. Larkin
*Attorney, Agent, or Firm*—Oblon, Spivak, McClelland, Maier & Neustadt, P.C.

[57] ABSTRACT

A container inspection apparatus inspects sealing performance of a closure of a container such as a bottle filled with effervescent beverage. The apparatus include a plurality of support members for placing a container thereon and movable along a certain path, a plurality of ultrasonic transducers fixed to one of the support members for generating ultrasonic vibration, and a supply device for supplying liquid to an upper surface of the support member. The ultrasonic vibration of the support member caused by the ultrasonic transducer is transmitted to a bottom of the container through liquid interposed between the bottom of the container and the upper surface of the support member. After vibrating the bottom of the container, beverage in the container is imaged by an imaging unit to detect a defective container which is not sealed properly.

8 Claims, 6 Drawing Sheets

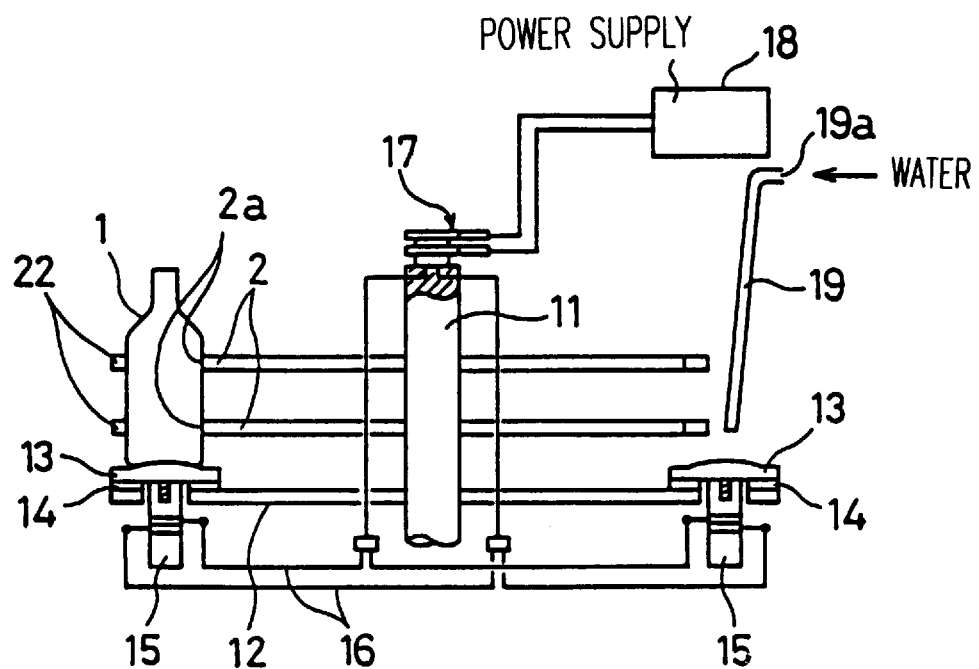
F I G. 2

CONTAINER INSPECTING APPARATUS

BACKGROUND OF THE INVENTION

1. Field of the Invention

The present invention relates to a container inspection apparatus, and more particularly to an apparatus for optically inspecting sealing performance of a closure of a container such as a bottle filled with an effervescent beverage. The effervescent beverage includes beer, carbonated drinks, and the like.

2. Description of the Prior Art

As an apparatus for inspecting sealing performance of a closure of a container, there has been known an apparatus which comprises means for causing a beverage to effervesce by applying ultrasonic vibration to the bottom of the container, and means for imaging liquid surface in the container and judging the container as a defective container which is not properly sealed when a large effervescent portion is detected at the liquid surface in the container. The conventional means for causing a beverage to effervesce comprises a net conveyor provided in a water tank and conveying containers while they are submerged in water in the water tank, and ultrasonic transducers provided at the bottom of the water tank. The ultrasonic transducers apply ultrasonic vibration to the bottoms of the containers on the net conveyor through water in the water tank. The containers are densely placed on the net conveyor in a staggered arrangement. The ultrasonic transducers are arranged at intervals to prevent mutual interference and in a plurality of rows which extend in a direction perpendicular to the traveling direction of the containers.

However, in the conventional means for causing a beverage to effervesce, the intensities of ultrasonic vibrations are not uniform in an entire area where the ultrasonic transducers are arranged, and hence some defective containers cannot be detected because of their small degrees of effervescence. Further, since the energy of ultrasonic vibration which is applied to the container per unit time is small, considerable time is required to allow a beverage to effervesce, thus requiring a large installation area for the container inspection apparatus.

SUMMARY OF THE INVENTION

It is therefore an object of the present invention to provide a container inspecting apparatus which enables an effervescent beverage such as beer in a container to effervesce reliably in a short time, and can detect defective sealing of a closure of a container without fail.

According to the present invention, there is provided an apparatus for inspecting sealing performance of a closure of a container filled with an effervescent beverage, comprising a plurality of support members each for placing a container thereon and being movable along a certain path; a plurality of ultrasonic transducers for generating ultrasonic vibration, each of the ultrasonic transducers being fixed to one of the support members; means for supplying liquid to an upper surface of the support member, ultrasonic vibration of the support member caused by the ultrasonic transducer being transmitted to a bottom of the container through liquid interposed between the bottom of the container and the upper surface of the support member; and an imaging unit for imaging the beverage in the container after vibrating the bottom of the container. The path of the support members is not within a water tank, i.e., it is in a non-liquid atmosphere. The liquid is therefore supplied locally to substantially only an upper surface of the support member.

With the above arrangement, since the ultrasonic transducer is fixed to the support member for placing the container thereon, the support member is vibrated together with the ultrasonic transducer. Simultaneously, liquid such as water is supplied to the upper surface of the support member, and hence vibration is transmitted from the support member to the bottom of the container through liquid. The vibration of the container causes the beverage in the container which is not properly sealed to effervesce, and therefore the defective container can be detected by imaging the effervescing portion of the beverage.

The above and other objects, features, and advantages of the present invention will become apparent from the following description when taken in conjunction with the accompanying drawings which illustrate a preferred embodiment of the present invention by way of example.

BRIEF DESCRIPTION OF THE DRAWINGS

FIG. 2 is a cross-sectional view taken along line II—II of FIG. 1;

DETAILED DESCRIPTION OF THE PREFERRED EMBODIMENT

A container inspecting apparatus which is an apparatus for inspecting sealing performance of a closure of a container such as a bottle according to a first embodiment of the present invention will be described below with reference to FIGS. 1 through 4.

Figure 1:
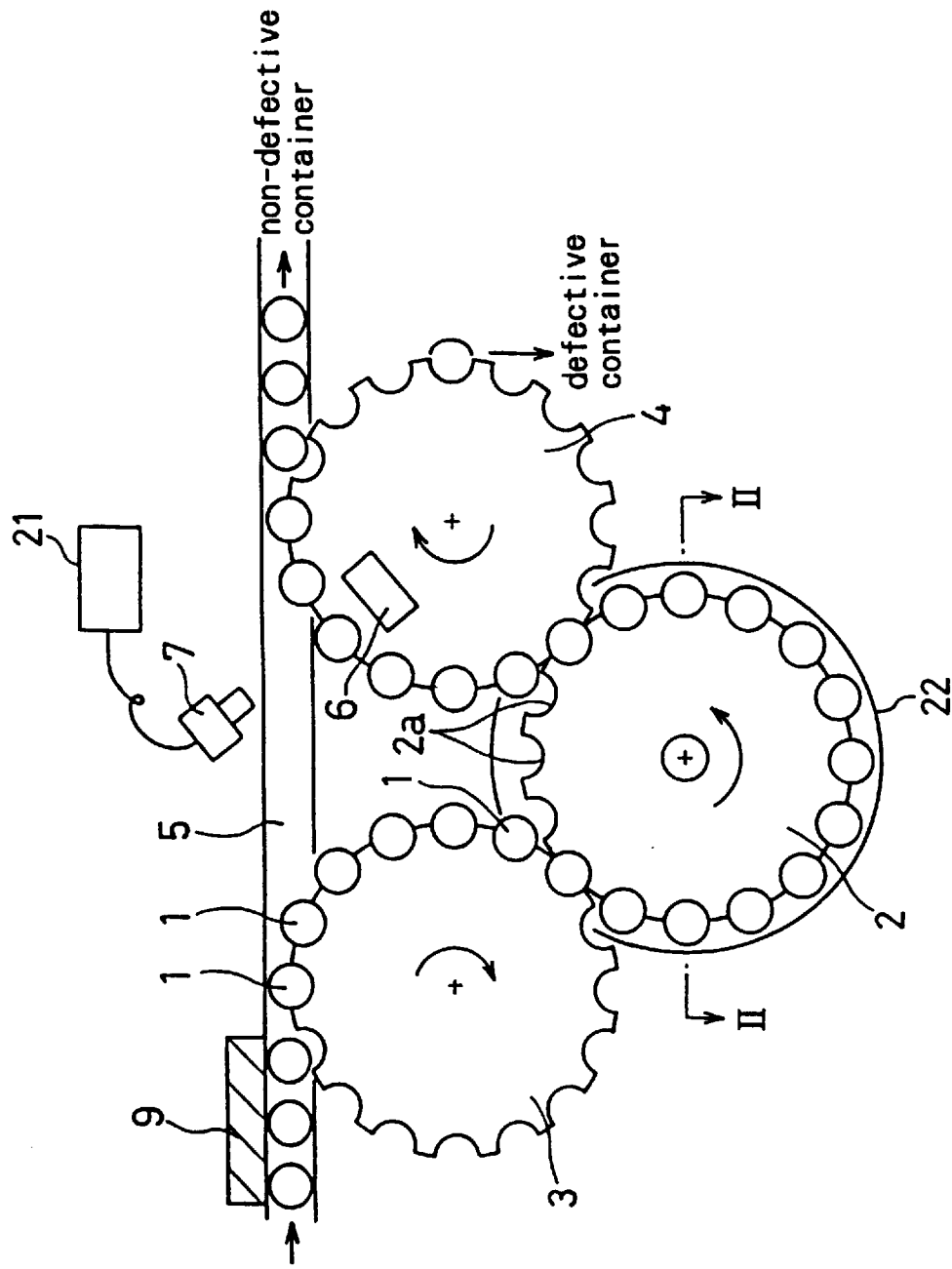
FIG. 1 is a plan view of a container inspecting apparatus according to a first embodiment of the present invention.

As shown in FIG. 1, the container inspecting apparatus comprises a main star wheel 2 for conveying a plurality of containers 1 along a circular path, an inlet star wheel 3 for successively supplying the containers 1 to the main star wheel 2, and an outlet star wheel 4 for successively discharging the containers 1 from the main star wheel 2.

A conveyor 5 is provided adjacent to the inlet star wheel 3 and the outlet star wheel 4, and an infeed screw 9 is disposed adjacent to the inlet star wheel 3. The containers 1, such as transparent glass bottles, are successively supplied from the conveyor 5 to the infeed screw 9 which causes the containers 1 to be spaced at constant intervals. Therefore, the containers 1 are transferred from the infeed screw 9 to the inlet star wheel 3 one by one, from which the containers 1 are transferred to the main star wheel 2. While the containers 1 are conveyed by the main star wheel 2, ultrasonic vibration is applied to each of the bottoms of the containers 1 to allow the beverage in each of the containers 1 to effervesce, and the containers 1 are then transferred to the outlet star wheel 4. An imaging unit comprising a lighting unit 6 and a camera 7, such as a CCD camera, is provided so as to position a circular path of the outlet star wheel 4 between the lighting unit 6 and the camera 7. The camera 7 is connected to an image processing device 21. While the container 1 is conveyed by the outlet star wheel 4, the container 1 is illuminated by the light unit 6, and the camera 7 takes an image of the container 1 with light transmitted through the container 1 to inspect the degree of effervescence of beverage in the container 1. The image obtained by the camera 7 is processed by the image processing device 21. Thereafter, the container 1 is returned to the conveyor 5 by the outlet star wheel 4.

FIG. 2 shows a detailed structure of a mechanism for causing the beverage to effervesce. As shown in FIGS. 1 and 2, the main star wheel 2 has a plurality of recesses 2a, at an outer periphery thereof, which engage the containers 1. The main star wheel 2 is supported by a main shaft 11 to which a turntable 12 is fixed. Movable support members 13 are provided coaxially with the recesses 2a, and the number of the movable support members 13 is equal to the number of the recesses 2a. Each of the movable support members 13 is fixed to the turntable 12 through a rubber plate 14. The movable support members 13 move along a circular path while they support the respective containers 1 thereon. During movement, the containers 1 are guided by guide rails 22 provided at the outer side of the main star wheel 2. An ultrasonic transducer 15 is fixed to each of the bottom surfaces of the movable support members 13. The ultrasonic transducer 15 is connected to a high-frequency power supply 18 through leads 16 and a slip ring 17. A tube 19 is disposed above the movable support member 13 to supply liquid such as water to the upper surface of the movable support member 13. The inlet 19a of the tube 19 is positioned at the outer side of the circular path of the movable support members 13.

Figure 3:
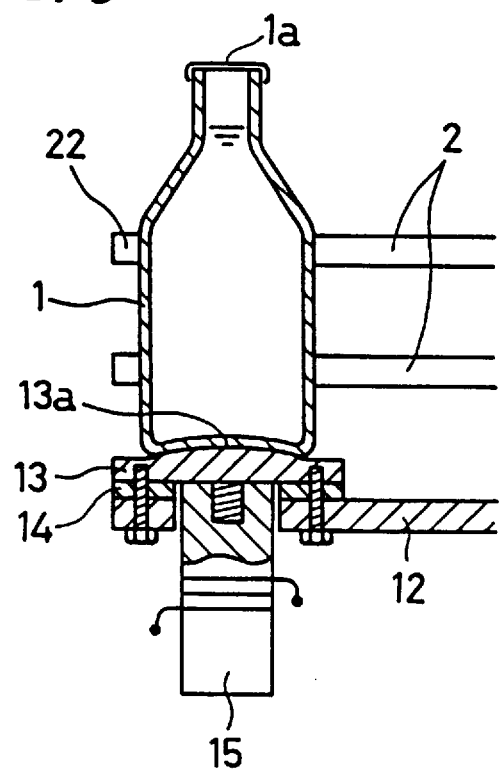
FIG. 3 is a cross-sectional view showing an essential part of FIG. 2.

FIG. 3 shows a detailed structure of the movable support member 13. The movable support member 13 is fixed to the turntable 12 by bolts, and the ultrasonic transducer 15 is fixed to the movable support member 13 by a screw engagement. The movable support member 13 has a convex upper surface 13a so as to correspond to the bottom shape of the container 1. As shown in FIG. 3, the container 1 is filled with an effervescent beverage, and the top of the container 1 is sealed tightly by a cap or a closure 1a.

Next, the operation of the container inspecting apparatus will be described below.

The containers 1 are successively supplied from the conveyor 5 to the main star wheel 2 through the infeed screw 9 and the inlet star wheel 3. The supplied containers 1 are placed on the respective movable support members 13 and conveyed along the circular path by the main star wheel 2. Before the containers 1 are placed on the movable support members 13, water is supplied from the tube 19 onto each of the upper surfaces 13a of the movable support members 13. Since the water is supplied from the tube 19, it is locally supplied to substantially only the upper surfaces 13a of the support members 13.

Figure 4A:
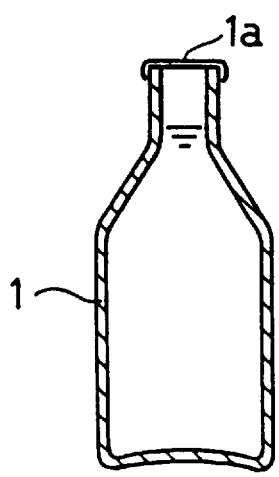
FIG. 4A is a cross-sectional view of a non-defective container.
Figure 4B:
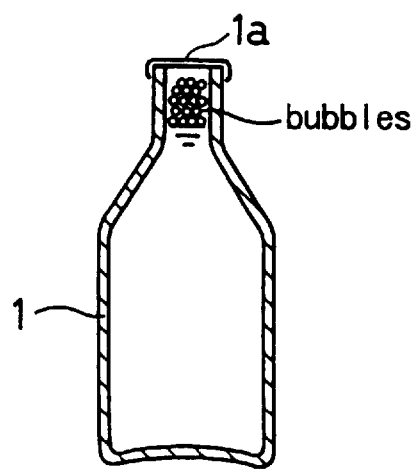
FIG. 4B is a cross-sectional view of a defective container.

While the containers 1 are conveyed by the main star wheel 2, the containers 1 are vibrated by the ultrasonic transducers 15. Since water is retained on the upper surfaces 13a of the movable support members 13, vibrations of the movable support members 13 are transmitted to the bottoms of the containers 1 through water interposed therebetween, respectively. Therefore, the effervescent beverage in each of the containers 1 is vibrated, and if the container 1 is properly sealed by the closure 1a, the beverage in the container 1 can hardly effervesce at the liquid surface as shown in FIG. 4A. However, if the container 1 is not sealed properly, the beverage in the container 1 effervesces intensely at the liquid surface as shown in FIG. 4B. That is, a number of bubbles are formed at the liquid surface and thereabout.

The liquid surface of the container 1 is imaged by the camera 7 immediately after the container 1 is transferred from the main star wheel 2 to the outlet star wheel 4. The camera 7 has a field of view which includes the surface of the container's level as well as bubbles. The image obtained by the camera 7 is processed by the image processing device 21, and the container 1 in which a large effervescent portion formed by a number of bubbles is detected at the liquid surface is judged as a defective container. The non-defective container is returned to the conveyor 5 by the outlet star wheel 4, but the defective container is discharged to a predetermined location by the outlet star wheel 4.

Figure 5A:
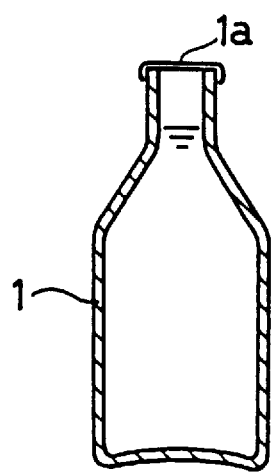
FIG. 5A is a cross-sectional view of a non-defective container.
Figure 5B:
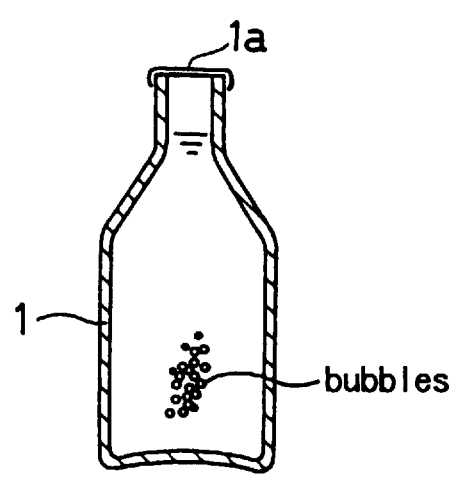
FIG. 5B is a cross-sectional view of a defective container.

In examples shown in FIGS. 4A and 4B, although the location to be imaged is the liquid surface of the beverage, the location to be imaged may be an intermediate portion below the liquid surface of the beverage. That is, if the container 1 is properly sealed by the closure 1a, the beverage in the container 1 can hardly effervesce at the intermediate portion below the liquid surface as shown in FIG. 5A. However, if the container 1 is not sealed properly, the beverage in the container 1 effervesces intensely at the intermediate portion below the liquid surface as shown in FIG. 5B. That is, a number of bubbles are formed at the intermediate portion of the beverage in the container 1. The intermediate portion of the beverage in the container 1 is imaged by the camera 7, and the container 1 in which a large effervescent portion formed by a number of bubbles is detected is judged as a defective container. This method can detect the effervescent portion earlier than the method of FIGS. 4A and 4B in which the liquid surface is imaged.

Figure 6:
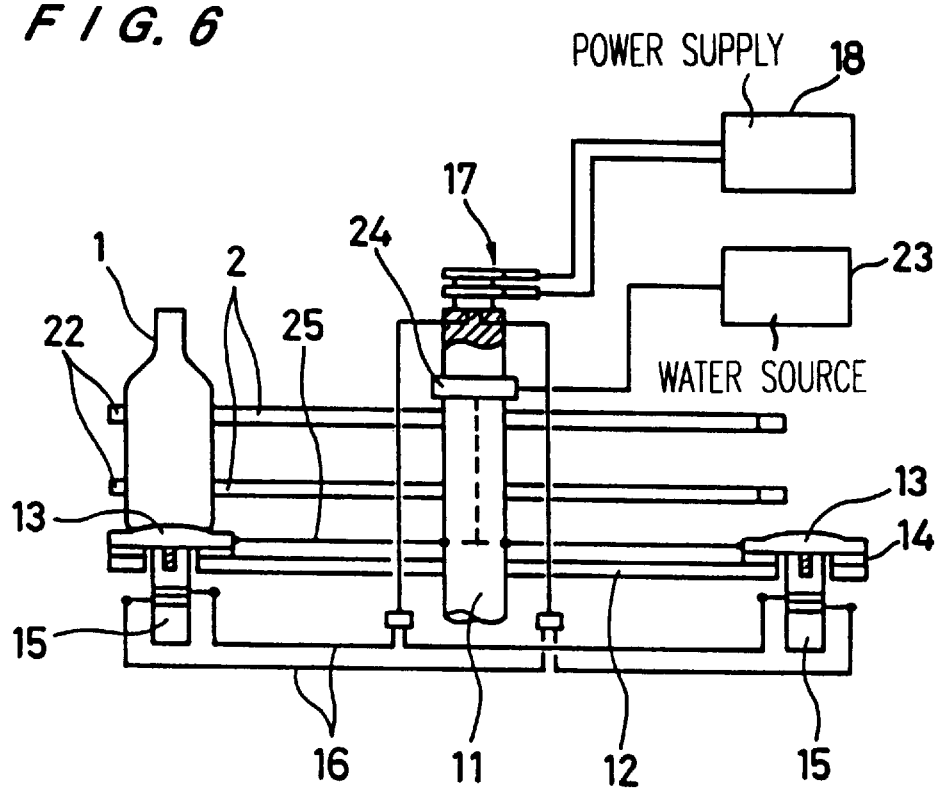
FIG. 6 is a cross-sectional view of a container inspecting apparatus according to a second embodiment of the present invention, and is a view corresponding to FIG. 2.
Figure 7:
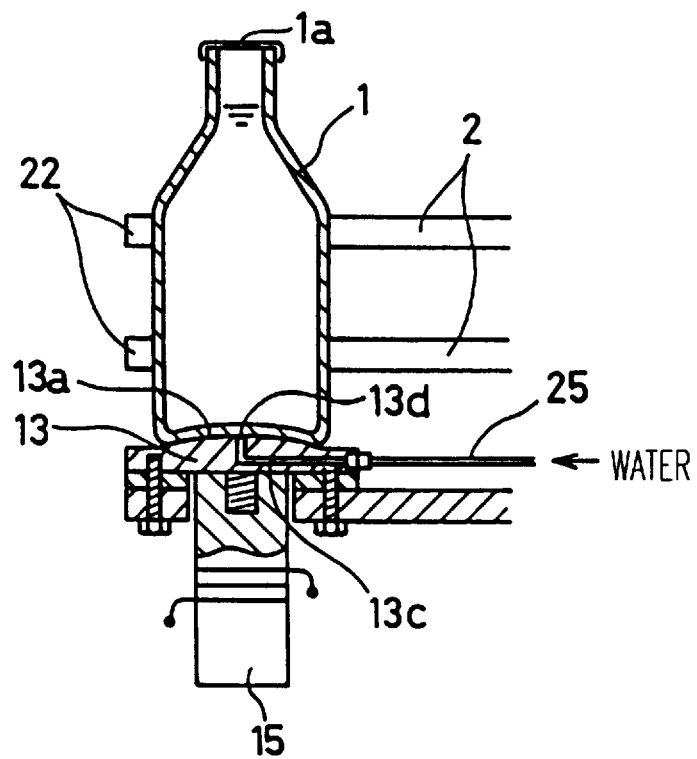
FIG. 7 is a cross-sectional view showing an essential part of FIG. 6.

FIGS. 6 and 7 show a second embodiment of the present invention. In this embodiment, as shown in FIG. 6, water is supplied from a pressurized water source 23 through a rotary seal 24 to the interior of the shaft 11 which supports the main star wheel 2. Water is supplied from the main shaft 11 to each of the movable support members 13 through a tube 25. As shown in FIG. 7, the movable support 13 has a passage 13c therein for allowing water to pass therethrough. Water supplied from the tube 25 to the passage 13c is ejected from an outlet port 13d to the outside.

According to this embodiment, water can be supplied to the upper surface 13a of the movable support member 13 in such a state that the container 1 is placed on the movable support member 13. The other details and operation of the container inspecting apparatus shown in FIGS. 6 and 7 are the same as the container inspecting apparatus shown in FIGS. 1 through 4.

Figure 8:
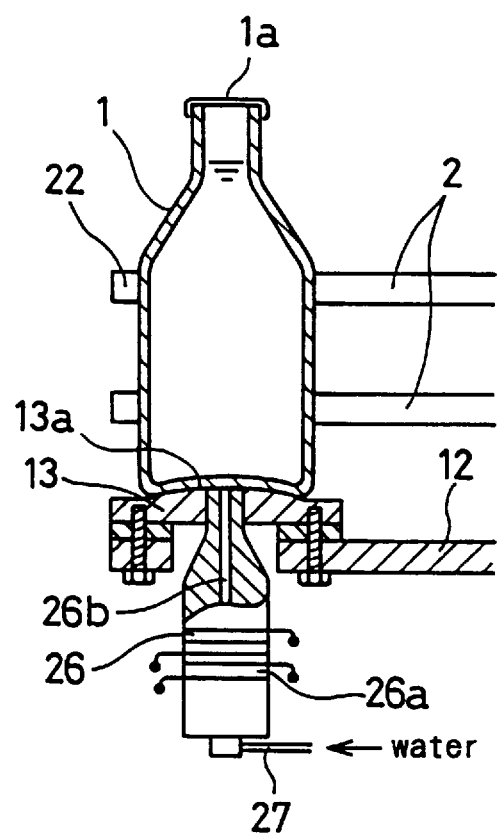
FIG. 8 is a cross-sectional view of a container inspecting apparatus according to a third embodiment of the present invention, and is a view corresponding to FIG. 7.

FIG. 8 shows a third embodiment of the present invention, and is a cross-sectional view corresponding to FIG. 7. In this embodiment, an ultrasonic transducer 26 having a horn-like body is fixed to the movable support member 13 by a screw engagement. The ultrasonic transducer 26 is provided at a lower portion thereof with a vibration detecting portion 26a comprising a piezoelectric element for detecting vibration of a vibration generating portion. The ultrasonic transducer 26 has a passage 26b therein for allowing water to pass therethrough. By supplying water from a tube 27 into the ultrasonic transducer 26, water is supplied from the upper end of the passage 26b to the upper surface 13a of the movable support member 13. The other details of this embodiment are the same as the embodiment shown in FIG. 7.

According to this embodiment, the ultrasonic transducer 26 has a tapered upper portion in the form of horn so that ultrasonic vibration converges on the upper portion of the ultrasonic transducer 26. Therefore, the beverage can effervesce in a short period of time. Further, since malfunction of the vibration generating portion in the ultrasonic transducer 26 can be detected by the vibration detecting portion 26a, the container inspecting apparatus can be shut off by a signal from the vibration detecting portion 26a.

In the embodiments, although the movable support member 13 moves along a circular path, it may move along a straight path or a curved path. Further, although the movable support member is vibrated by the ultrasonic transducer, it may be vibrated by any other vibrating means.

As is apparent from the above description, according to the present invention, since the containers can be placed one by one on the respective movable support members which are vibrated, if the containers are not sealed properly, the effervescent beverage in the containers can effervesce without fail and in a short time. Therefore, a defective container in which any leaks exist can be detected reliably, and the container inspecting apparatus becomes compact.

Although a certain preferred embodiment of the present invention has been shown and described in detail, it should be understood that various changes and modifications may be made therein without departing from the scope of the appended claims.

What is claimed is:

1. An apparatus for inspecting sealing performance of a closure of containers filled with an effervescent beverage, comprising:

a plurality of support members each for placing a container thereon and being movable along a certain path in a non-liquid atmosphere;

a plurality of ultrasonic transducers for generating ultrasonic vibration, each of said ultrasonic transducers being fixed to one of said support members;

means for supplying liquid to an upper surface of said support members, ultrasonic vibration of said support members caused by said ultrasonic transducers being transmitted to bottoms of said containers through liquid interposed between said bottoms of said containers and said upper surfaces of said support members; and an imaging unit for imaging th beverage in said containers after vibrating said bottoms of said containers.

2. The apparatus according to claim 1, wherein said upper surfaces of said support members have a convex shape so as to correspond to said bottoms of said containers.

3. The apparatus according to claim 1, wherein said imaging unit images the liquid surface of said beverage in said containers.

4. The apparatus according to claim 1, wherein said imaging unit images an intermediate portion of said beverage in said containers.

5. The apparatus according to claim 1, wherein said ultrasonic transducers each comprises a vibration generating portion and a vibration detecting portion for detecting vibration of said vibration generating portion.

6. The apparatus according to claim 1, wherein said ultrasonic transducers each has a tapered upper portion in the form of horn.

7. The apparatus according to claim 1, wherein said ultrasonic transducers each has a passage therein for allowing liquid to pass therethrough.

8. An apparatus for inspecting sealing performance of a closure of containers filled with an effervescent beverage, comprising:

a plurality of support members each for placing a container thereon and being movable along a certain path;

a plurality of ultrasonic transducers for generating ultrasonic vibration, each of said ultrasonic transducers being fixed to one of said support members;

means for locally supplying liquid to substantially only an upper surface of said support members, ultrasonic vibration of said support members caused by said ultrasonic transducers being transmitted to bottoms of said containers through the liquid interposed between said bottoms of said containers and said upper surfaces of said support members; and an imaging unit for imaging the beverage in said containers after vibrating said bottoms of said containers.

* * * * *